(12) United States Patent
Murayama et al.

(10) Patent No.: US 8,007,447 B2
(45) Date of Patent: Aug. 30, 2011

(54) GUIDE WIRE

(75) Inventors: Hiraku Murayama, Shizuoka (JP); Akihiko Umeno, Shizuoka (JP); Jun Iwami, Shizuoka (JP); Yutaka Itou, Shizuoka (JP); Youki Aimi, Shizuoka (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 142 days.

(21) Appl. No.: 12/463,596

(22) Filed: May 11, 2009

(65) Prior Publication Data

US 2009/0221935 A1 Sep. 3, 2009

Related U.S. Application Data

(62) Division of application No. 10/634,845, filed on Aug. 6, 2003, now Pat. No. 7,547,288.

(30) Foreign Application Priority Data

| Aug. 8, 2002 | (JP) | 2002-232162 |
| Dec. 6, 2002 | (JP) | 2002-355909 |
| May 30, 2003 | (JP) | 2003-156012 |

(51) Int. Cl.
*A61M 25/00* (2006.01)
(52) U.S. Cl. ...................................................... 600/585
(58) Field of Classification Search .................. 600/585, 600/300, 407, 431, 433, 434, 435; 604/19, 604/27, 48, 93.01, 95.04, 103.09, 103.1, 604/164.01, 164.13
See application file for complete search history.

(56) References Cited

U.S. PATENT DOCUMENTS

| 4,884,579 A | 12/1989 | Engelson |
| 4,925,445 A | 5/1990 | Sakamoto et al. |
| 5,111,829 A | 5/1992 | Alvarez de Toledo |
| 5,171,383 A | 12/1992 | Sagae et al. |
| 5,341,817 A | 8/1994 | Viera |
| 5,341,818 A | 8/1994 | Abrams et al. |
| 5,358,796 A | 10/1994 | Nakamura et al. |
| 5,365,943 A | 11/1994 | Jansen |

(Continued)

FOREIGN PATENT DOCUMENTS

EP 0 806 220 A2 11/1997

(Continued)

OTHER PUBLICATIONS

Notice of Reason for Refusal according to Japanese Patent Application No. 2003-156012 (w/English Translation) dated Dec. 18, 2007.

(Continued)

*Primary Examiner* — Jeffrey G Hoekstra
(74) *Attorney, Agent, or Firm* — Buchanan Ingersoll & Rooney PC

(57) ABSTRACT

A guide wire includes a first wire disposed on the distal side of the guide wire and a second wire disposed on the proximal side. The second wire has an elastic modulus larger than the first wire. The first wire is joined to the second wire at a welded portion by welding. A coil is disposed on the distal side of the first wire. A cover layer is formed on the outer peripheral surface of the wire member in such a manner as to cover at least the welded portion. The cover layer is made from a material capable of reducing the friction of the cover layer, for example, a fluorocarbon resin or a hydrophilic material, to thereby improve the sliding performance of the guide wire. Such a guide wire is excellent in operationality and kink resistance.

21 Claims, 8 Drawing Sheets

U.S. PATENT DOCUMENTS

| | | |
|---|---|---|
| 5,368,661 A | 11/1994 | Nakamura et al. |
| 5,411,476 A | 5/1995 | Abrams et al. |
| 5,701,911 A | 12/1997 | Sasamine et al. |
| 5,722,424 A | 3/1998 | Engelson |
| 5,769,796 A | 6/1998 | Palermo et al. |
| 5,772,609 A | 6/1998 | Nguyen et al. |
| 6,001,068 A | 12/1999 | Uchino et al. |
| 6,019,737 A | 2/2000 | Murata |
| 6,039,700 A | 3/2000 | Sauter |
| 6,193,706 B1 | 2/2001 | Thorud et al. |
| 6,251,086 B1 | 6/2001 | Cornelius et al. |
| 6,402,706 B2 | 6/2002 | Richardson et al. |
| 6,488,637 B1 | 12/2002 | Eder et al. |
| 6,494,847 B1 | 12/2002 | Richardson et al. |
| 6,544,197 B2 | 4/2003 | DeMello |
| 2001/0009980 A1 | 7/2001 | Richardson et al. |
| 2001/0011158 A1 | 8/2001 | Howland |
| 2001/0023319 A1 | 9/2001 | Miyata et al. |
| 2002/0032390 A1 | 3/2002 | Jafari |
| 2002/0046785 A1 | 4/2002 | Abrams et al. |
| 2002/0087099 A1 | 7/2002 | Nanis et al. |
| 2003/0069521 A1 | 4/2003 | Reynolds et al. |
| 2003/0125641 A1 | 7/2003 | Jafari et al. |
| 2005/0101836 A1 | 5/2005 | Onuki et al. |

FOREIGN PATENT DOCUMENTS

| | | |
|---|---|---|
| EP | 0 838 230 A2 | 4/1998 |
| JP | 1-124473 | 5/1989 |
| JP | 04-009162 | 1/1992 |
| JP | 08-004727 | 1/1996 |
| JP | 10-057499 | 3/1998 |
| JP | 10-118005 | 5/1998 |
| JP | 10-328157 A | 12/1998 |
| JP | 2001-340288 | 12/2001 |
| JP | 2002-017863 A | 1/2002 |

OTHER PUBLICATIONS

Notice of Reason for Refusal according to Japanese Patent Application No. 2003-156011 (w/English Translation) dated Dec. 18, 2007.

Official Action (Notification of Reason for Refusal) issued by the Japanese Patent Office in corresponding JP 2003-156012, May 27, 2008, JPO, JP: and English-language translation thereof.

F I G. 2 A
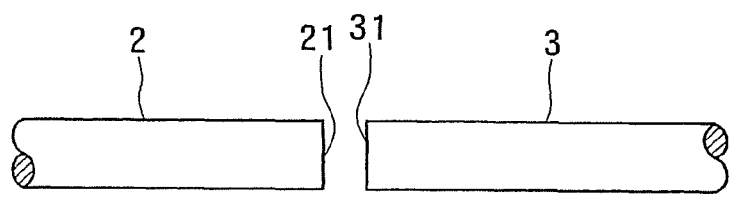
F I G. 2 B
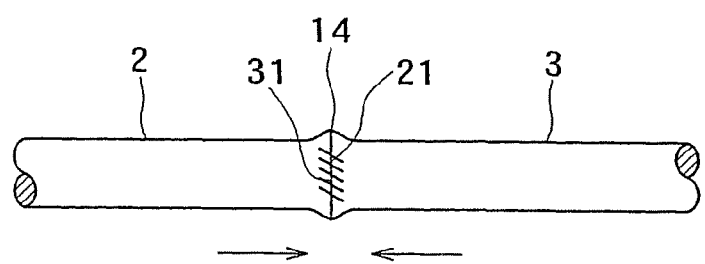
F I G. 2 C
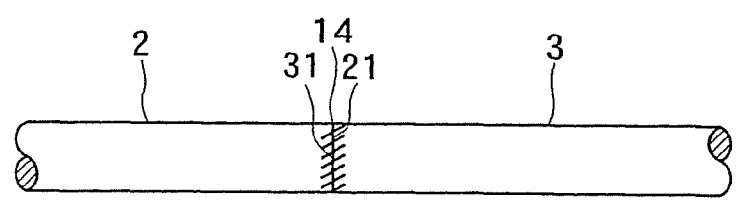
F I G. 2 D
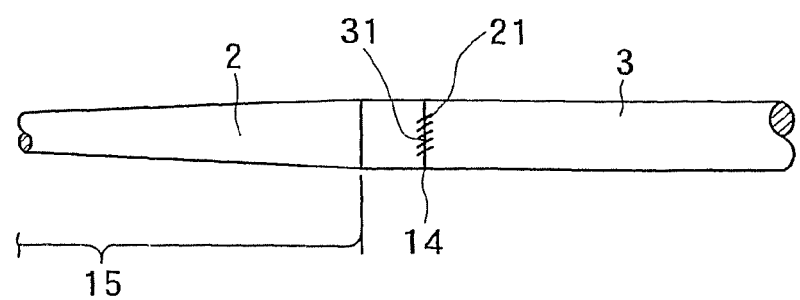

F I G. 9
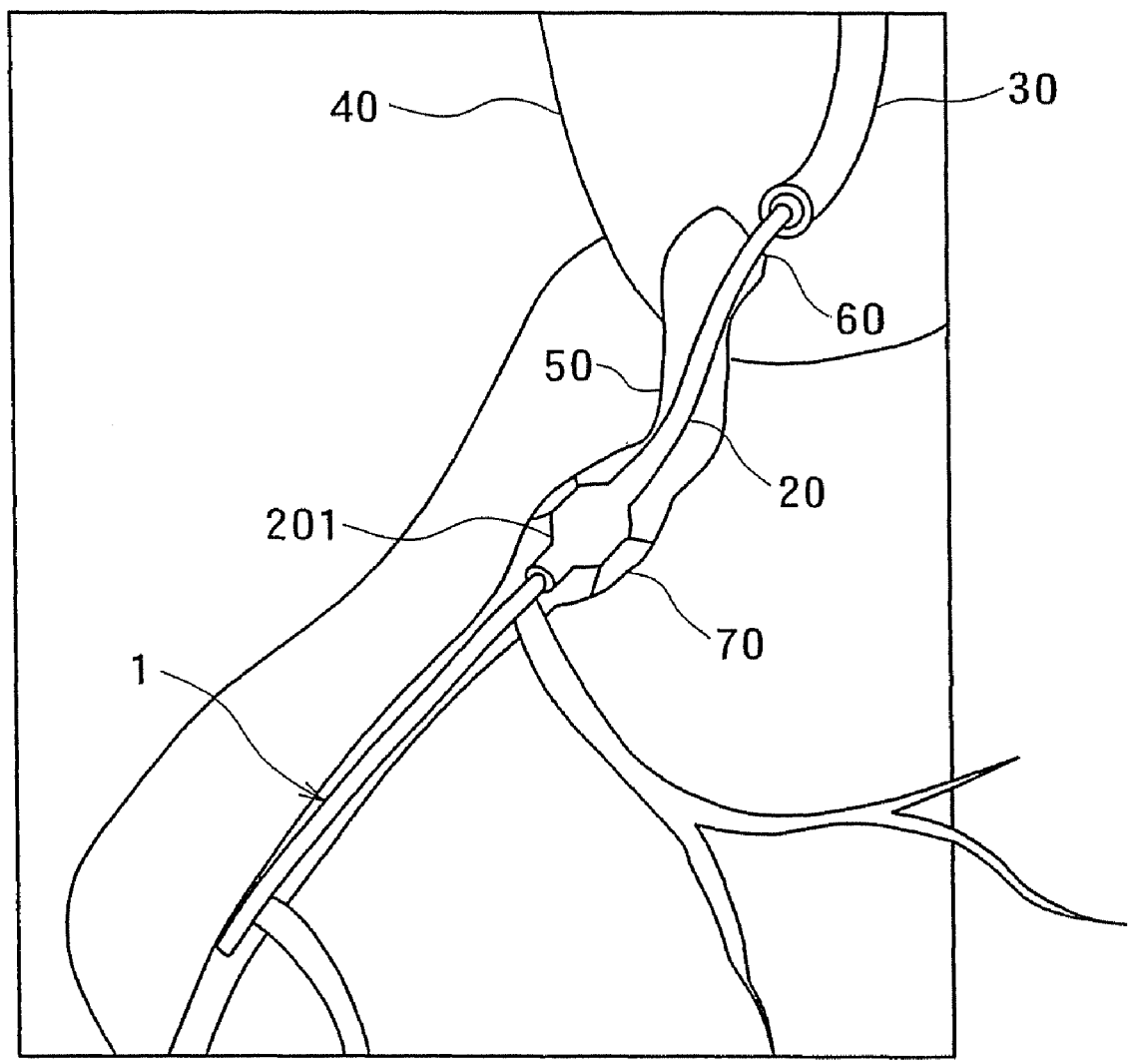

GUIDE WIRE

This application is a divisional of U.S. application Ser. No. 10/634,845 filed on Aug. 6, 2003, the entire contents of which is incorporated by reference herein, and claims priority to Japanese Patent Application No. 2002-232162 filed on Aug. 8, 2002, Japanese Patent Application No. 2002-355909 filed on Dec. 6, 2002, and Japanese Patent Application No. 2003-156012 filed on May 30, 2003, the entire contents of each of which is incorporated by reference herein.

BACKGROUND OF THE INVENTION

1. Field of the Invention

The present invention relates to a guide wire, particularly to a guide wire used to guide a catheter in a body lumen such as a blood vessel.

2. Description of the Related Art

Guide wires are used to guide a catheter in treatment of cites at which open surgeries are difficult or which require minimally invasiveness to the body, for example, PTCA (Percutaneous Transluminal Coronary Angioplasty), or in examination such as cardio-angiography. A guide wire used in the PTCA procedure is inserted, with the distal end projecting from the distal end of a balloon catheter, into the vicinity of a target angiostenosis portion together with the balloon catheter, and is operated to guide the distal end portion of the balloon catheter to the target angiostenosis portion.

A guide wire used to insert a catheter into a blood vessel complicatedly bent requires appropriate flexibility and restoring performance against bending, pushability and torque transmission performance (generically called "operationality") for transmitting an operational force from the proximal end portion to the distal side, and kink resistance (often called "resistance against sharp bending"). To obtain appropriate flexibility as one of the above-described performances, there has been known a guide wire configured such that a metal coil having flexibility is provided around a small-sized core member at the distal end of the guide wire, or a guide wire including a core member made from a superelastic material such as an Ni—Ti alloy for improving the flexibility and restoring performance.

Conventional guide wires include a core member that is substantially made from a single material. In particular, to enhance the operationality of the guide wire, a material having a relatively high elastic modulus is used as the material of the core member. The guide wire including such a core member, however, has an inconvenience that the distal end portion of the guide wire becomes lower in flexibility. On the other hand, if a material having a relatively low elastic modulus is used as the material of the core member for increasing the flexibility of the distal end portion of the guide wire, the operationality of the proximal end portion of the guide wire is degraded. In this way, it has been regarded as difficult to satisfy both requirements associated with the flexibility and operationality by using a core member made from a single material.

A guide wire intended to solve such a problem has been disclosed, for example, in U.S. Pat. No. 5,171,383, wherein a Ni—Ti alloy wire is used as a core member, and the distal side and the proximal side of the alloy wire are heat-treated under different conditions in order to enhance the flexibility of the distal end portion of the alloy wire while enhancing the rigidity of the proximal side of the alloy wire. Such a guide wire, however, has a problem that the control of the flexibility of the distal end portion by heat-treatment has a limitation. For example, even if it is successful to obtain a sufficient flexibility of the distal end portion of the alloy wire, it may often fail to obtain a sufficient rigidity on the proximal side of the alloy wire.

SUMMARY OF THE INVENTION

An object of the present invention is to provide a guide wire excellent in operationality and kink resistance.

To achieve the above object, according to a first aspect of the present invention, there is provided a guide wire including a wire member including a welded portion formed by welding a first wire disposed on the distal side of the wire body to a second wire disposed on the proximal side from the first wire and made from a material having an elastic modulus larger than that of the first wire, the welded portion being made substantially smooth, and a cover layer provided on the outer periphery of the wire body covering at least the welded portion between the first wire and the second wire.

According to a second aspect of the present invention, there is provided a guide wire including a wire member including a welded portion formed by welding a first wire disposed on the distal side of the wire member to a second wire disposed on the proximal side from the first wire and made from a material having an elastic modulus larger than that of the first wire, and a cover layer provided on the outer periphery of the wire body in covering at least the welded portion between the first wire and the second wire, wherein the welded portion has a projection projecting in the outer peripheral direction.

According to a third aspect of the present invention, there is provided a guide wire including a wire member including a welded portion formed by welding a first wire disposed on the distal side of the wire member to a second wire disposed on the proximal side from the first wire and made from a material having an elastic modulus larger than that of the first wire, and a cover layer provided on the outer periphery of the wire covering at least the welded portion between the first wire and the second wire, and a distal-side cover layer disposed on the distal side from the cover layer, the distal-side cover layer being made from a material different from that of the cover layer.

In the above guide wire, preferably, the cover layer is formed in such a manner that the wire body is substantially not heated at the time of covering the wire body with the cover layer, and the distal-side cover layer is formed in such a manner that the wire body is heated at the time of covering the wire body with the distal-side cover layer.

According to a fourth aspect of the present invention, there is provided a guide wire including a wire member including a welded portion formed by welding a first wire disposed on the distal side of the wire member to a second wire disposed on the proximal side from the first wire and made from a material having an elastic modulus larger than that of the first wire, and a cover layer provided on the outer periphery of the wire body covering at least the welded portion between the first wire and the second wire, and a proximal-side cover layer disposed on the proximal side from the cover layer, the proximal-side cover layer being made from a material different from that of the cover layer.

In the above guide wire, preferably, the cover layer is formed in such a manner that the wire body is substantially not heated at the time of covering the wire body with the cover layer, and the proximal-side cover layer is formed in such a manner that the wire body is heated at the time of covering the wire body with the proximal-side cover layer.

The distal-side cover layer may be made from a material capable of reducing the friction of the distal-side cover layer.

In particular, the distal-side cover layer is preferably made from a fluorocarbon resin or hydrophilic material.

The average thickness of the distal-side cover layer is preferably in a range of 1 to 20 μm.

The proximal-side cover layer may be made from a material capable of reducing the friction of the proximal-side cover layer. In particular, the proximal-side cover layer is preferably made from a fluorocarbon resin or hydrophilic material.

The average thickness of the proximal-side cover layer is preferably in a range of 1 to 20 μm.

The welded portion preferably has a projection projecting in the outer peripheral direction.

The second wire preferably has, in the vicinity of the welded portion, a portion with its cross-sectional area smaller than that of a proximal end portion of the first wire.

The cover layer may be made from a material capable of reducing the friction of the cover layer. In particular, the cover layer is preferably made from a fluorocarbon resin or hydrophilic material.

The cover layer is preferably made from a silicone resin. The cover layer preferably functions as a reinforcing layer for reinforcing the welded portion.

The cover layer is preferably made from a metal material. The cover layer is preferably made from a material having rigidity equal to or smaller than that of a material for forming the first wire.

The average thickness of the cover layer is preferably in a range of 1 to 20 μm. The thickness of the cover layer is preferably nearly uniform.

The thickness of a portion, which covers at least the welded portion, of the cover layer is preferably nearly uniform.

The cover layer is preferably provided in such a manner as to cross the welded portion, and to have a thickness nearly uniform from the proximal end to the distal end of the welded portion.

The cover layer is preferably provided in such a manner as to cross the projection, and to have a thickness nearly uniform from the proximal end to the distal end of the projection.

The wire body preferably has an outer-diameter gradually reducing portion with its outer diameter gradually reduced in the direction toward the distal end of the wire body.

The guide wire preferably has a spiral coil provided so as to cover at least a distal end portion of the first wire. The welded portion is preferably located on the proximal side from the proximal end of the coil.

The guide wire preferably has a second cover layer provided so as to cover at least part of the coil.

The first wire is preferably made from a superelastic alloy. The second wire is preferably made from a stainless steel.

The second wire is preferably made from a Co-based alloy. The Co-based alloy is preferably a Co—Ni—Cr alloy.

A connection end face of the first wire to the second wire and a connection end face of the second wire to the first wire are preferably set to be each substantially perpendicular to the axial direction of the first and second wires. The welding between the first wire and the second wire is preferably performed by a butt resistance welding process.

The projection is preferably formed at the time of welding the first wire and the second wire to each other.

The guide wire is preferably used in such a manner that the welded portion is located in a living body.

As described above, since the guide wire of the present invention has the first wire disposed on the distal side and the second wire disposed on the proximal side from the first wire and made from a material having an elastic modulus larger than that of the first wire, it is possible to ensure a high rigidity at a proximal end portion while keeping a high flexibility at a distal end portion, and hence to enhance the pushability, torque transmission performance, and trackability of the guide wire.

Since the first wire and the second wire are joined to each other by welding, it is possible to enhance the joining strength of the joining portion (welded portion), and hence to certainly transmit a torsional torque or pushing force from the second wire to the first wire.

Since the cover layer is provided on the outer periphery of the wire body in such a manner as to cover at least the welded portion, even if stepped portions or burrs occur on the outer peripheral surface of the welded portion, the stepped portions or burrs can be covered with the cover layer. As a result, it is possible to prevent or relieve an adverse effect caused by the stepped portions or burrs.

In the case of providing the cover layer made from a silicone resin, it is possible to ensure a sufficient sliding performance of the entire guide wire while keeping a high joining strength between the first wire and the second wire at the time of forming the cover layer, and hence to enhance the operationality of the guide wire.

In the case of providing the cover layer made from a material capable of reducing the friction of the cover layer, it is possible to improve the sliding performance of the guide wire in a catheter or the like, and hence to further enhance the operationality of the guide wire. Since the sliding resistance of the guide wire is reduced, it is possible to more certainly prevent kink (sharp bending) or torsion of the guide wire, particularly, in the vicinity of the welded portion.

In the case of providing the cover layer functioning as a reinforcing layer for reinforcing the welded portion, it is possible to further enhance the joining strength between the first wire and the second wire. Accordingly, when a torsional torque or pushing force is applied from the second wire to the first wire, it is possible to more certainly transmit the torsional torque or pushing force without deformation or breakage of the welded portion.

In the case of providing the second cover layer, the distal-side cover layer, and the proximal-side cover layer, which are different from the cover layer, it is possible to provide a local portion at which the sliding resistance is larger than that of the cover layer, and hence to facilitate the placement of the guide wire.

Since the projection is formed at the welded portion, it is possible to further enhance the joining strength of the joining portion (welded portion), and hence to more certainly transmit a torsional torque or pushing force from the second wire to the first wire.

BRIEF DESCRIPTION OF THE DRAWINGS

These and other objects, features, and advantages of the present invention will become more apparent from the following detailed description in conjunction with the accompanying drawings, wherein:

FIGS. 2A to 2D are views showing steps of a procedure for connecting a first wire and a second wire of the guide wire shown in FIG. 1;

FIG. 9 is a typical view illustrating the example of how to use the guide wire of the present invention.

DETAILED DESCRIPTION OF THE PREFERRED EMBODIMENTS

A guide wire of the present invention will now be described in detail by way of preferred embodiments shown in the accompanying drawings.

Figure 1:
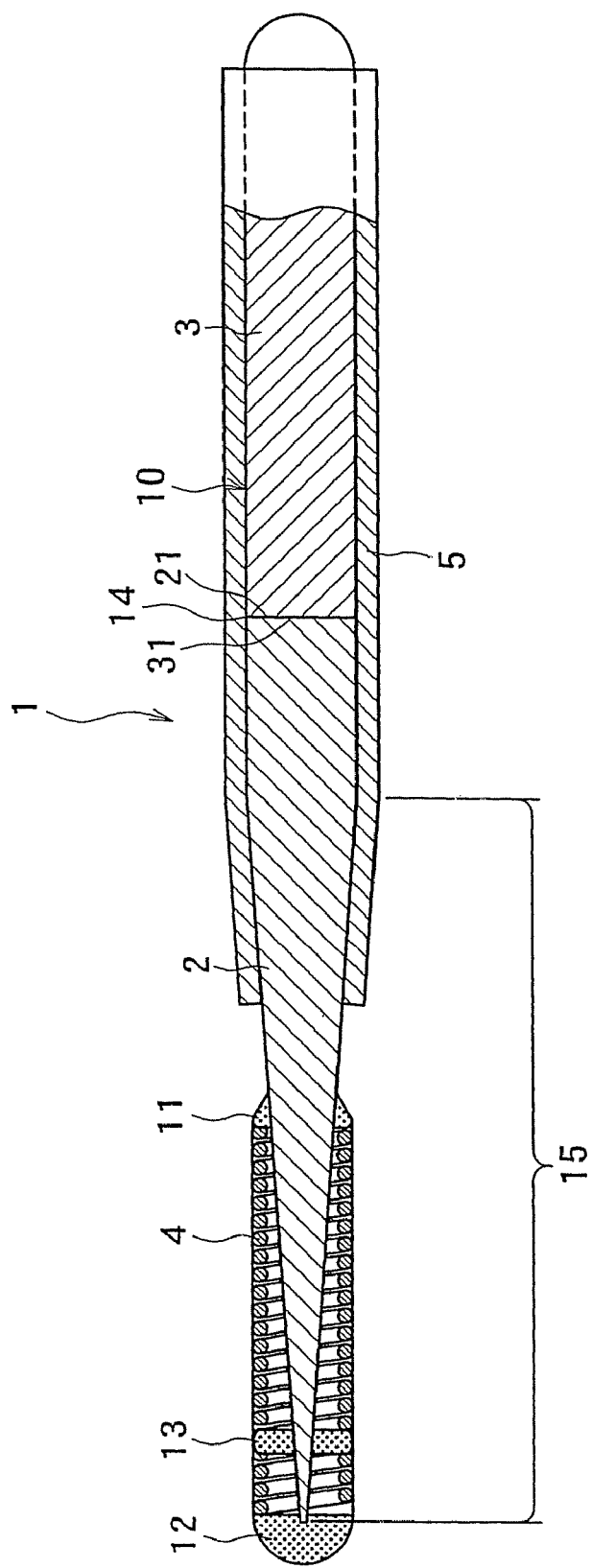
FIG. 1 is a longitudinal sectional view showing a first embodiment of a guide wire of the present invention.
Figure 3:
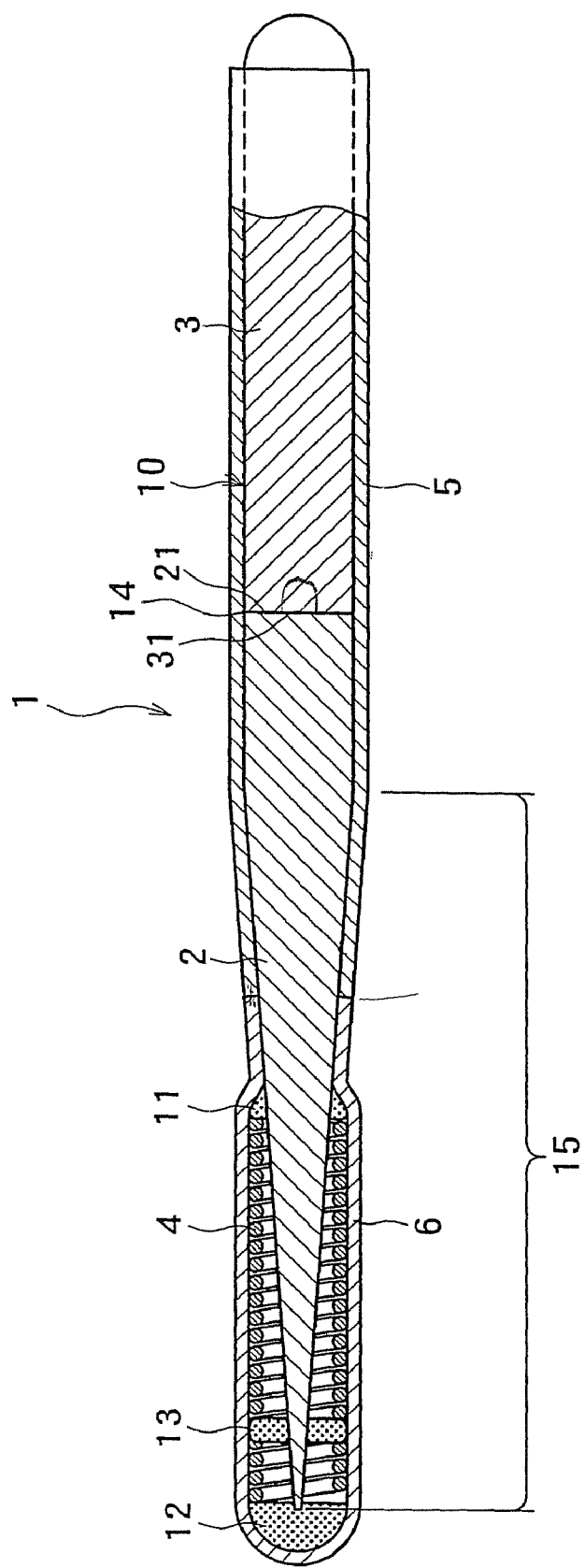
FIG. 3 is a longitudinal sectional view showing a second embodiment of the guide wire of the present invention.

FIG. 1 is a longitudinal sectional view of a first embodiment of a guide wire of the present invention, FIGS. 2A to 2D are views showing a procedure for joining a first wire and a second wire of the guide wire shown in FIG. 1 to each other, and FIG. 3 is a longitudinal sectional view showing a second embodiment of the guide wire of the present invention. For convenience of description, the right side in FIG. 1 and FIGS. 2A to 2D is taken as the "proximal side" and the left side in FIG. 1 and FIGS. 2A to 2D is taken as the "distal side". It is to be noted that in FIG. 1 and FIGS. 2A to 2D, for easy understanding, the dimension of the guide wire in the thickness direction is exaggeratedly enlarged while the dimension of the guide wire in the length direction is shortened, and therefore, the ratio of the thickness to the length is significantly different from the actual ratio. The same is true for FIGS. 3 to 5 to be described later.

A guide wire 1 shown in FIG. 1 is of a type used to be inserted in a catheter, and includes a wire member 10 and a spiral coil 4. The wire member 10 is formed by joining a first wire 2 disposed on the distal side to a second wire 3 disposed on the proximal side from the first wire 2. The entire length of the guide wire 1 is not particularly limited but is preferably in a range of about 200 to 5,000 mm. The outer diameter of a constant outer-diameter portion of the wire member 10 is not particularly limited but is preferably in a range of about 0.2 to 1.2 mm.

The first wire 2 is configured as a wire having elasticity. The length of the first wire 2 is not particularly limited but is preferably in a range of about 20 to 1,000 mm.

According to this embodiment, the first wire 2 has an outer-diameter constant portion extending for a specific length from the proximal end, and an outer-diameter gradually reducing portion 15 extending from the outer-diameter constant portion to the distal end. The outer-diameter of the outer-diameter gradually reducing portion 15 is gradually reduced in the direction toward the distal end. The provision of the outer-diameter gradually reducing portion 15 is effective to gradually reduce the rigidity (flexural rigidity, torsional rigidity) of the first wire 2 in the direction toward the distal end. As a result, the distal end portion of the guide wire 1 has a high flexibility, to improve trackability and safety to a blood vessel and to prevent sharp-bending and the like.

In the configuration shown in the figure, the outer-diameter gradually reducing portion 15 is formed as part of the first wire 2; however, such a portion 15 may be formed as the whole of the first wire 2. The taper angle (reduction ratio of the outer-diameter) of the outer-diameter gradually reducing portion 15 may be constant or partially changed in the longitudinal direction of the first wire 2. For example, portions in each of which the taper angle (reduction ratio of the outer diameter) is relatively large and portions in each of which the taper angle is relatively small may be alternately repeated by a plurality of numbers.

The first wire 2 may be configured such that a portion with its outer diameter is kept constant in the longitudinal direction be located at a middle portion of the outer-diameter gradually reducing portion 15 or on the distal side from the outer-diameter gradually reducing portion 15. For example, the first wire 2 may be configured such that a plurality of taper portions in each of which the outer diameter is gradually reduced in the direction toward the distal end be formed in the longitudinal direction and a portion in which the outer diameter is kept constant in the longitudinal direction be formed between adjacent two of the taper portions. The first wire 2 having such a configuration can exhibit the same effect as that described above.

Unlike the configuration shown in the figure, the proximal end of the outer-diameter gradually reducing portion 15 may be located at a middle point of the second wire 3, and more specifically, the outer-diameter gradually reducing portion 15 may be formed so as to cross the boundary (welded portion 14 to be described later) between the first wire 2 and the second wire 3.

The material for forming the first wire 2 is not particularly limited but may be selected from metal materials such as stainless steels. In particular, alloys having pseudo-elasticity (for example, superelastic alloys) are preferable, and superelastic alloys are more preferable. Superelastic alloys are relatively flexible, good in restoring performance, and less susceptible to reforming. Accordingly, if the first wire 2 is made from a superelastic alloy, the guide wire 1 including such a first wire 2 has, at its distal portion, a high flexibility and a high restoring performance against bending, and a high trackability to a blood vessel complicatedly curved or bent, to thereby enhance the operationality of the guide wire 1. Even if the first wire 2 is repeatedly deformed, that is, curved or bent, the first wire 2 is no or less plastic deforming because of its high restoring performance. This prevents degradation of the operationality due to the plastic deforming of the first wire 2 during use of the guide wire 1.

Pseudo-elastic alloys include those of a type in which the stress-strain curve in a tensile test has any shape, those of a type in which a transformation point such as As, Af, Ms, or Mf can be significantly measured or not measured, and those of all types in which the shape is greatly deformed by stress and then restored nearly to an original shape by removal of stress.

Examples of superelastic alloys include Ni—Ti alloys such as an Ni—Ti alloy containing Ni in an amount of 49-52 atomic %, a Cu—Zn alloy containing Zn in an amount of 38.5 to 41.5 wt %, a Cu—Zn—X alloy containing X in an amount of 1 to 10 wt % (X: at least one kind selected from a group consisting of Be, Si, Sn, Al, and Ga), and an Ni—Al alloy containing Al in an amount of 36 to 38 atomic %. Of these materials, the Ni—Ti alloy is preferable. In addition, a superelastic alloy represented by a Ni—Ti alloy is excellent in adhesion against a cover layer 5 or a second cover layer 6.

The distal end of the second wire 3 is joined to the proximal end of the first wire 2 at a welded portion 14 by welding. The second wire 3 is a wire member having elasticity. The length of the second wire 3 is not particularly limited but may be in a range of about 20 to 4,800 mm.

The second wire 3 is made from a material having an elastic modulus (Young's modulus or modulus of longitudinal elasticity, modulus of rigidity or modulus of transverse elasticity, or bulk modulus) larger than that of the first wire 2. The second wire 3 can thus exhibit an appropriate rigidity (flexural rigidity, torsional rigidity). As a result, the guide wire 1 becomes firm, to improve the pushability and torque transmission performance, thereby enhancing the operationality at the time of insertion of the guide wire 1.

The material for forming the second wire 3 is not particularly limited but may be selected from metal materials, for example, stainless steels (all kinds specified in SUS, for example, SUS304, SUS303, SUS316, SUS316L, SUS316J1, SUS316J1L, SUS405, SUS430, SUS434, SUS444, SUS429, SUS430F, and SUS302), piano wire steels, cobalt alloys, and alloys having pseudo-elasticity.

In particular, cobalt alloys are preferably used for the second wire 3. This is because the second wire 3 made from a cobalt alloy has a high elastic modulus and an appropriate elastic limit. Such a second wire 3 exhibits a good torque transmission performance, thereby hardly causing a problem associated with buckling or the like. Any type of cobalt alloy may be used insofar as it contains cobalt. In particular, a cobalt alloy containing cobalt as a main component (that is, a cobalt-based alloy containing cobalt in an amount [in wt %] being the largest among the contents of all components of the alloy) is preferably used, and further, a Co—Ni—Cr alloy is more preferable. The use of the cobalt alloy having such a composition as the material for forming the second wire 3 is effective to further enhance the above-described effects. The cobalt alloy having such a composition is also advantageous in that since the alloy exhibits plasticity in deformation at room temperature, the second wire 3 made from such a cobalt alloy is easily deformable into a desired shape, for example, during use of the guide wire. A further advantage of the cobalt alloy having such a composition is as follows: namely, since the second wire 3 made from such a cobalt alloy has a high elastic modulus and is cold-formable even if it exhibits a high elastic limit, the second wire 3 can be thinned while sufficiently preventing occurrence of buckling, and therefore, can exhibit a high flexibility and a high rigidity enough to be inserted into a desired site.

The Co—Ni—Cr alloy is exemplified by an alloy containing 28-50 wt % of Co, 10-30 wt % of Ni, and 10-30 wt % of Cr, the balance being Fe. In this alloy, part of any component may be substituted by another element (substitution element). The incorporation of such a substitution element exhibits an effect inherent to the kind thereof. For example, the incorporation of at least one kind selected from a group consisting of Ti, Nb, Ta, Be, and Mo further improves the strength of the second wire 3. In the case of incorporating one or more substitution elements other than Co, Ni, and Cr, the total content of the substitution elements is preferably in a range of 30 wt % or less.

For example, part of Ni may be substituted by Mn, which is effective to further improve the workability. Part of Cr may be substituted by Mo and/or W, which is effective to further improve the elastic limit. Of the Co—Ni—Cr alloys, a Co—Ni—Cr—Mo alloy is particularly preferable.

Examples of compositions of the Co—Ni—Cr alloys include (1) 40 wt % Co-22 wt % Ni-25 wt % Cr-2 wt % Mn-0.17 wt % C-0.03 wt % Be—Fe (balance), (2) 40 wt % Co-15 wt % Ni-20 wt % Cr-2 wt % Mn-7 wt % Mo-0.15 wt % C-0.03 wt % Be—Fe (balance), (3) 42 wt % Co-13 wt % Ni-20 wt % Cr-1.6 wt % Mn-2 wt % Mo-2.8 wt % W-0.2 wt % C-0.04 wt % Be—Fe (balance), (4) 45 wt % Co-21 wt % Ni-18 wt % Cr-1 wt % Mn-4 wt % Mo-1 wt % Ti-0.02 wt % C-0.3 wt % Be—Fe (balance), and (5) 34 wt % Co-21 wt % Ni-14 wt % Cr-0.5 wt % Mn-6 wt % Mo-2.5 wt % Nb-0.5 wt % Ta—Fe (balance). The wording "Co—Ni—Cr alloy" used herein is the conception including these Co—Ni—Cr alloys.

If a stainless steel is used as the material for forming the second wire 3, the pushability and torque transmission performance can be further enhanced.

The first wire 2 and the second wire 3 may be made from different alloys, and particularly, the first wire 2 is preferably made from a material having an elastic modulus smaller than that of the material of the second wire 3. With this configuration, the distal end portion of the guide wire 1 has a high flexibility, and the proximal end portion of the guide wire 1 has a high rigidity (flexural rigidity, torsional rigidity). As a result, the guide wire 1 has a high pushability and a high torque transmission performance, thereby enhancing the operationality, and also exhibits, on the distal side, a high flexibility and a high restoring performance, thereby improving trackability and safety to a blood vessel.

As one preferred combination of materials of the first wire 2 and the second wire 3, the first wire 2 is made from a superelastic alloy and the second wire 3 is made from a Co—Ni—Cr alloy or a stainless steel. With this configuration, the above-described effects become more significant.

In the configuration shown FIG. 1, the second wire 3 has a nearly constant outer diameter over the entire length; however, the second wire 3 may have portions with outer diameters changed in the longitudinal direction.

From the viewpoint of enhancing the flexibility and restoring performance of the distal end portion of the first wire 2, it is preferred to use a Ni—Ti alloy as the superelastic alloy for forming the first wire 2.

The coil 4 is a member formed by spirally winding a wire, especially fine filamentous wire, and is provided so as to cover the distal end portion of the first wire 2. In the configuration shown in FIG. 1, the distal end portion of the first wire 2 is disposed in an approximately axially center portion of the coil 4 in such a manner as to be not in contact with the inner surface of the coil 4. In addition, the welded portion 4 is located on the proximal side from the proximal end of the coil 4.

It is to be noted that in the configuration shown in FIG. 1, the coil 4 is loosely disposed in such a manner that a slight gap remains between adjacent spirally wound wire portions in a state that no external force is applied to the coil 4; however, the coil 4 may be tightly disposed in such a manner that no gap remains between the adjacent spirally wound wire portions in a state that no external force is applied to the coil 4.

The coil 4 may be made from a metal material such as a stainless steel, a superelastic alloy, a cobalt alloy, a noble metal such as gold, platinum, or tungsten, or an alloy containing such a noble metal. In particular, the coil 4 is preferably made from a radiopaque material such as a noble metal. If the coil 4 is made from such a radiopaque material, the guide wire 1 can exhibit an X-ray contrast performance. This makes it possible to insert the guide wire 1 in a living body while confirming the position of the distal end portion of the guide wire 1 under fluoroscopy. The distal side and proximal side of the coil 4 may be made from different alloys. For example, the distal side of the coil 4 may be formed of a coil made from a radiopaque material and the proximal side of the coil 4 be formed of a coil made from a relatively radiolucent material such as a stainless material. The entire length of the coil 4 is not particularly limited but may be in a range of about 5 to 500 mm.

The proximal end portion and the distal end portion of the coil 4 are fixed to the first wire 2 by a fixing material 11 and a fixing material 12, respectively, and an intermediate portion (close to the distal end) of the coil 4 is fixed to the first wire 2 by a fixing material 13. Each of the fixing materials 11, 12, and 13 is a solder (brazing material). Alternatively, each of the fixing materials 11, 12, and 13 may be an adhesive. In addition, in place of using the fixing material, the coil 4 may be fixed to the first wire 2 by welding. To prevent damage of the inner wall of a blood vessel, the leading end surface of the fixing material 12 is preferably rounded.

According to this embodiment, since the first wire 2 is partially covered with the coil 4, the contact area of the first wire 2 with the inner wall of a catheter used together with the guide wire 1 is small, with a result that it is possible to reduce the sliding resistance of the guide wire 1 in the catheter. This is effective to further improve the operationality of the guide wire 1.

In this embodiment, the wire having a circular shape in cross-section is used for the coil 4; however, the cross-sectional shape of the wire used for the coil 4 may be another shape such as an elliptic shape or a quadrilateral shape (especially, rectangular shape).

In the guide wire 1, the first wire 2 and the second wire 2 are joined to each other by welding. The welded portion (joining portion) 14 between the first wire 2 and the second wire 3 has a high joining strength, to allow a torsional torque or pushing force to be certainly transmitted from the second wire 3 to the first wire 2.

The outer peripheral portion of the welded portion 14 is preferably made substantially smooth, for example, in accordance with steps 3 and 4 of a procedure of joining the first wire 1 to the second wire 2 by welding (to be described later).

In this embodiment, a connection end face 21 of the first wire 2 to the second wire 3 and a connection end face 31 of the second wire 3 to the first wire 2 are each formed into a plane nearly perpendicular to the axial (longitudinal) direction of both the wires 2 and 3. This significantly facilitates working for forming the connection end faces 21 and 31, to achieve the above-described effects without complicating the steps for producing the guide wire 1.

It is to be noted that each of the connection end faces 21 and 31 may be tilted relative to the plane perpendicular to the axial (longitudinal) direction of both the wires 2 and 3, or formed into a recessed or raised shape.

The method of welding the first wire 2 and the second wire 3 to each other is not particularly limited but is generally exemplified by spot welding using laser or butt resistance welding such as butt seam welding. In particular, to ensure a high joining strength of the welded portion 14, butt resistance welding is preferable.

The procedure of joining the first wire 2 and the second wire 3 to each other by butt seam welding as one example of butt resistance welding will be described with reference to FIGS. 2A to 2D. FIGS. 2A to 2D show steps 1 to 4 of the procedure of joining the first wire 2 and the second wire 3 to each other by butt seam welding.

In the step 1, the first wire 2 and the second wire 3 are fixed (mounted) to a butt welder (not shown).

In the step 2, the connection end face 21 on the proximal side of the first wire 2 and the connection end face 31 on the distal side of the second wire 3 are butted to each other while a specific voltage is applied thereto by the butt welder. With this operation, a fused layer (welded surface) is formed at the contact portion, whereby the first wire 2 and the second wire 3 are strongly joined to each other.

In the step 3, a projection of the joining portion (welded portion 14), formed by deformation of the joining portion upon butt welding, is removed, with a result that the outer periphery of the welded portion 14 is made substantially smooth. The removal of the projection may be performed by polishing, grinding, or chemical treatment such as etching.

In the step 4, a portion, on the distal side from the joining portion (welded portion 14), of the first wire 2 is polished or ground, to form the outer-diameter gradually reducing portion 15 with its outer diameter gradually reduced in the direction toward the distal end.

If the proximal end of the outer-diameter gradually reducing portion 15 is set on the proximal side from the welded portion 14, the procedure may be jumped from the step 2 to the step 4, with the step 3 omitted.

The wire member 10 has a cover layer 5 that covers the whole or part of the outer surface (outer peripheral surface). The cover layer 5 can be formed for satisfying various purposes, one of which is to reduce the friction (sliding resistance) of the guide wire 1 for improving the sliding performance of the guide wire 1, thereby enhancing the operationality of the guide wire 1.

To satisfy the above-described purpose, the cover layer 5 is preferably made from a material capable of reducing the friction of the guide wire 1. With this configuration, since the friction resistance (sliding resistance) of the guide wire 1 against the inner wall of a catheter used together with the guide wire 1 is reduced, the sliding performance of the guide wire 1 is improved, to enhance the operationality of the guide wire 1 in the catheter. Further, since the sliding resistance of the guide wire 1 is reduced, it is possible to more certainly prevent, at the time of movement and/or rotation of the guide wire 1 in the catheter, kink (sharp bending) or torsion of the guide wire 1, particularly, in the vicinity of a welded portion of the guide wire 1.

Examples of the materials capable of reducing the friction of the guide wire 1 include polyorefins such as polyethylene and polypropylene, polyvinyl chloride, polyesters (such as PET and PBT), polyamide, polyimide, polyurethane, polystyrene, polycarbonate, silicone resins, fluorocarbon resins (such as PTFE and ETFE), and composite materials thereof.

In particular, the use of a fluorocarbon resin or a composite material thereof as the material for forming the cover layer 5 is advantageous in effectively reducing the friction resistance (sliding resistance) of the guide wire 1 having such a cover layer 5 against the inner wall of a catheter, to improve the sliding performance, thereby enhancing the operationality of the guide wire 1 in the catheter.

Further, in the case of moving and/or rotating the guide wire 1 having such a cover layer 5 in the catheter, it is possible to more certainly prevent kink (sharp bending) or torsion of the guide wire, particularly, in the vicinity of the welded portion 14.

The formation of the cover layer 5 using a fluorocarbon resin or a composite material thereof is generally performed by heating the fluorocarbon resin and covering the wire member 10 with the fluorocarbon resin, for example, in accordance with a baking process or spraying process. Such a covering process is effective to significantly enhance the adhesion of the cover layer 5 with the wire member 10.

In the case of using a silicone resin or a composite material thereof as the material for forming the cover layer 5, it is possible to form the cover layer 5 certainly, strongly adhering on the wire member 10 without the need of heating the silicone resin. To be more specific, by using a silicone resin of a reaction-curing type or a composite material thereof, the formation of the cover layer 5 can be performed at room temperature. The formation of the cover layer 5 at room temperature is advantageous not only in realizing simple coating but also sufficiently keeping the joining strength of the welded portion 14 between the first wire 2 and the second wire 3 without thermal degradation of the welded portion 14.

A hydrophilic material or a hydrophobic material can be also used as another preferred example of the material capable of reducing the friction of the guide wire 1. In particular, the hydrophilic material is preferable.

Examples of the hydrophilic materials include a cellulose based polymer, a polyethylene oxide based polymer, a maleic anhydride based polymer (for example, a maleic anhydride copolymer such as methylvinylether-maleic anhydride copolymer), an acrylic amide based polymer (for example, polyacrylic amide or polyglycidyl methacrylate-dimethyl acrylic amide [PGMA-DMAA] block copolymer), water-soluble nylon, polyvinyl alcohol, and polyvinyl pyrolidone.

In many cases, the hydrophilic material can exhibit a lubricating performance in a wet (water-absorbing) state. The use of the cover member 5 made from such a hydrophilic material is effective to reduce the friction resistance (sliding resistance) of the guide wire 1 against the inner wall of a catheter used together with the guide wire 1, to improve the sliding performance of the guide wire 1, thereby enhancing the operationality of the guide wire 1 in the catheter.

The cover layer 5 may be formed in such a manner as to cover the whole or part of the wire member 10 in the longitudinal direction. In particular, the cover layer 5 is preferably formed so as to cover the welded portion 14, and specifically, formed in a region including the welded portion 14. With this configuration, even if stepped portions or burrs may occur on the outer peripheral portion of the welded portion 14, such stepped portions or burrs are covered with the covered layer 5, whereby a sufficient sliding performance can be ensured. Also, since the cover layer 5 has a nearly uniform outer diameter, the sliding performance can be further improved.

The thickness (in average) of the cover layer 5 is not particularly limited but is preferably in a range of about 1 to 20 μm, more preferably, about 2 to 10 μm. If the thickness of the cover layer 5 is less than the lower limit, the effect obtained by formation of the cover layer 5 may be not sufficiently achieved and the cover layer 5 may be often peeled. If the thickness of the cover layer 5 is more than the upper limit, the physical properties of the wire may be obstructed and the cover layer 5 may be often peeled.

According to the present invention, the outer peripheral surface of the wire member 10 may be subjected to a treatment (such as chemical treatment or heat treatment) for improving the adhesion characteristic of the cover layer 5, or may be provided with an intermediate layer for improving the adhesion characteristic of the cover layer 5.

A second embodiment of the guide wire of the present invention will be described with reference to FIG. 3, principally, about differences from the first embodiment, with the description of the same features omitted.

A guide wire 1 shown in FIG. 3 is configured such that the distal end of a cover layer 5 is located on the proximal side from the proximal end of a coil 4, and a second cover layer 6 different from the cover layer 5 is formed on the distal side from the cover layer 5.

The second cover layer 6 is provided so as to cover the whole or part of the coil 4. In the configuration shown in the figure, the second cover layer 6 covers the whole of the coil 4.

The second cover layer 6 may be made from a material selected from the above-described materials used for forming the cover layer 5 and other materials, for example, polyorefins such as polyethylene and polypropylene, polyvinyl chloride, polyesters (such as PET and PBT), polyamide, polyimide, polyurethane, polystyrene, polycarbonate, fluorocarbon resins, silicone resins, silicone rubbers, and various kinds of elastomers (for example, thermoplastic elastomers such as polyamide-based elastomer and polyester-based elastomer).

The material for forming the second cover layer 6 may be identical to or different from the material for forming the cover layer 5.

The materials for forming the cover layer 5 and the second cover layer 6 are not particularly limited as described above, but are preferably set such that a silicone resin or a composite material be used for forming the cover layer 5 and a fluorocarbon resin or a composite material thereof be used for forming the second cover layer 6.

With this configuration, it is possible to combine the above-described advantage obtained by the use of a silicone resin with an advantage obtained by the use of a fluorocarbon resin. Concretely, by adopting such a combination of the materials of the cover layer 5 and the second cover layer 6, it is possible to obtain a sufficient sliding performance of the entire guide wire 1 while keeping the joining strength of the welded portion 14 between the first wire 2 and the second wire 3, and hence to enhance the operationality of the guide wire 1.

In the case of using a silicone resin or a composite material thereof for forming the cover layer 5 and also using a fluorocarbon resin or a composite material for forming the second cover layer 6, it is preferred that the wire member 10 be not heated for forming the cover layer 5 as described above and be heated for forming the second cover layer 6. With this configuration, it is possible to make the above-described effect significant and to enhance the adhesion of the second cover layer 6 with the wire member 10.

In the case of using a hydrophobic resin for forming the cover layer 5 and also using a hydrophilic resin for forming the second cover layer 6, it is possible to improve the sliding performance in a catheter and to enhance crossability in a blood vessel.

The thickness (in average) of the second cover layer 6 is not particularly limited but is preferably in a range of about 1 to 20 μm, more preferably, about 2 to 10 μm. The thickness of the second cover layer 6 may be identical to or different from that of the cover layer 5.

The guide wire of the present invention may be not provided with the coil 4. In this case, the second cover layer 6 may be provided or not provided at the position where the coil 4 is omitted.

In the configuration shown in FIG. 3, the distal end of the cover layer 5 is joined to the proximal end of the second cover layer 6, and is therefore continuous thereto; however, the distal end of the cover layer 5 may be separated from the proximal end of the second cover layer 6, or the cover layer 5 may be partially overlapped to the second cover layer 6.

Figure 4:
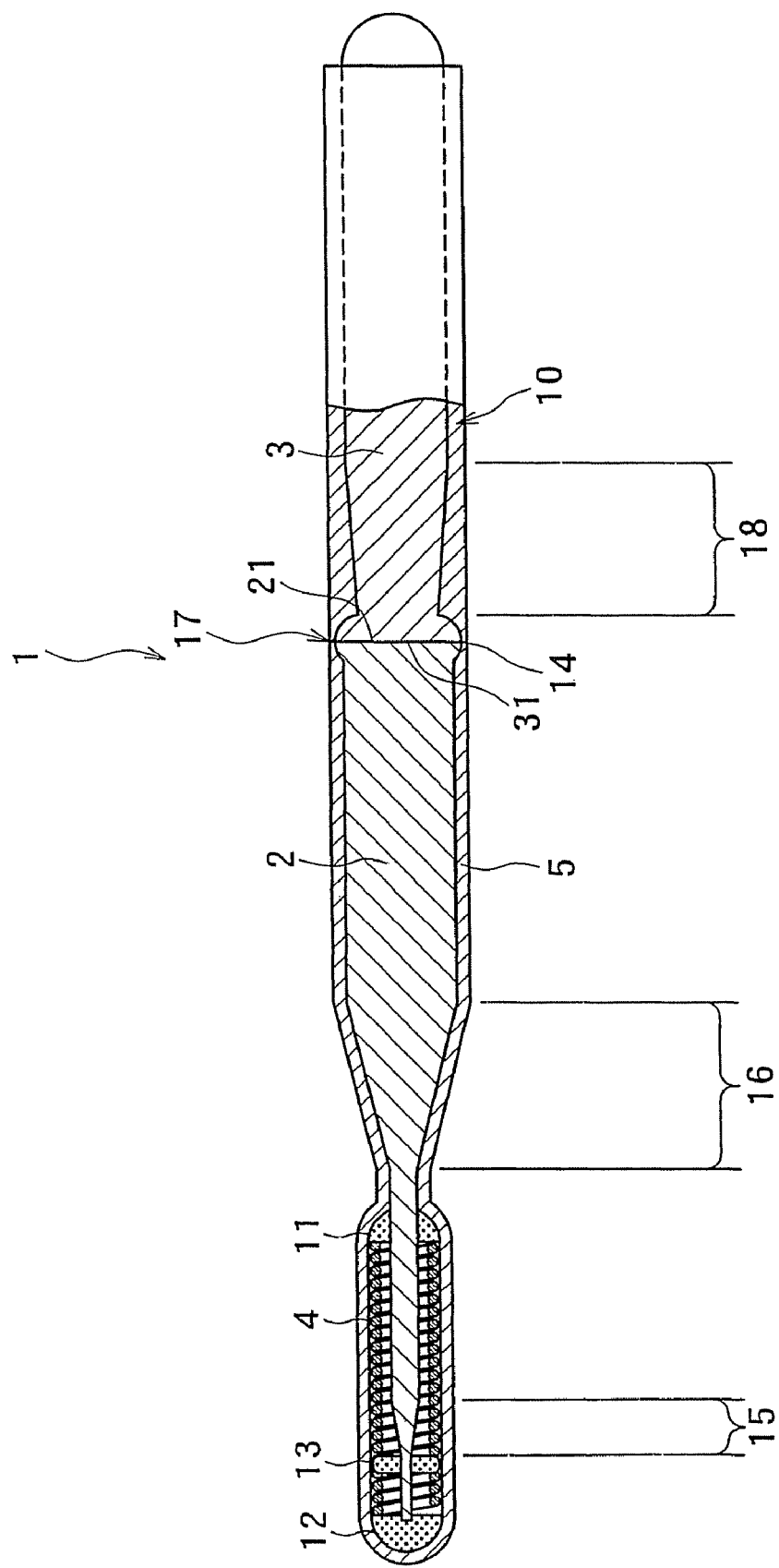
FIG. 4 is a longitudinal sectional view showing a third embodiment of the guide wire of the present invention.

FIG. 4 is a longitudinal sectional view showing a third embodiment of the guide wire of the present invention. The third embodiment of the guide wire of the present invention will be described with reference to FIG. 4, principally, about differences from the previous embodiments, with the description of the same features omitted.

According to a guide wire 1 in this embodiment, a first wire 2 has an outer-diameter gradually reducing portion 15 and an outer-diameter gradually reducing portion 16 provided on the proximal side from the outer-diameter gradually reducing portion 15. In this way, the first wire 2 (or second wire 3) may have outer-diameter gradually reducing portions at a plurality of positions.

According to the guide wire 1 in this embodiment, the second wire 3 has an outer-diameter gradually reducing portion 18 in the vicinity of the distal end thereof. To be more specific, the second wire 3 has a first portion provided in the vicinity of the distal end and a second portion provided on the proximal side from the first portion, wherein the second portion has rigidity higher than that of the first portion. This gives rise to an effect of making transition of elasticity between the first wire 2 and the second wire 3 smooth.

In this embodiment, a welded portion 14 has a projection 17 projecting in the outer peripheral direction. The formation of such a projection 17 is effective to enlarge a joining area between the first wire 2 and the second wire 3, and hence to significantly enhance the joining strength. This is advantageous in more certainly transmitting a torsional torque or pushing force from the second wire 3 to the first wire 2.

The formation of the projection 17 may make the welded portion 14 between the first wire 2 and the second wire 3 easily visible under fluoroscopy. As a result, it is possible to easily, certainly recognize the advancing state of the guide wire 1 and a catheter in a blood vessel or the like by checking the fluoroscopic image, and hence to shorten the operation time and to improve the safety.

The height of the projection 17 is not particularly limited but is preferably in a range of 0.001 to 0.3 mm, more preferably, 0.005 to 0.05 mm. If the height of the projection 17 is less than the lower limit, it may fail to sufficiently obtain the above-described effects depending on the materials of the first wire 2 and the second wire 3. If the height of the projection 17 is more than the upper limit, since the inner diameter of a lumen, in which the guide wire 1 is to be inserted, of a balloon catheter is fixed, the outer diameter of the second wire 3 on the proximal side must be thin relative to the height of the projection 17, with a result that it may become difficult to ensure sufficient physical properties of the second wire 3.

The projection 17 can be formed by smoothly shaping the projection in the step 3 of the above-described procedure of joining the first wire 2 to the second wire 3 (see FIG. 2). In particular, in the case where the second wire 2 has the outer-diameter gradually reducing portion (small cross-sectional area portion) 18 as in the guide wire 1 according to this embodiment, the projection 17 can be formed by welding the first wire 2 to the second wire 3 having a cross-sectional area gradually reducing (small cross-sectional area portion) with its cross-sectional area gradually reduced in the direction toward the distal end by the above-described procedure.

A cover layer 5 covers the outer-diameter gradually reducing portion 18 and the projection 17 and has a substantially uniform outer diameter. The term "substantially uniform outer diameter" contains an outer diameter smoothly changed within such a range as not to cause any inconvenience in use of the guide wire.

In this embodiment, the cover layer 5 covers a region including the coil 4, the first wire 2, and the second wire 3; however, the cover layer 5 may be formed so as to cover the first wire 2 and the second wire 3, and the coil 4 be covered with a material different from the cover layer 5, for example, a hydrophilic material.

Figure 5:
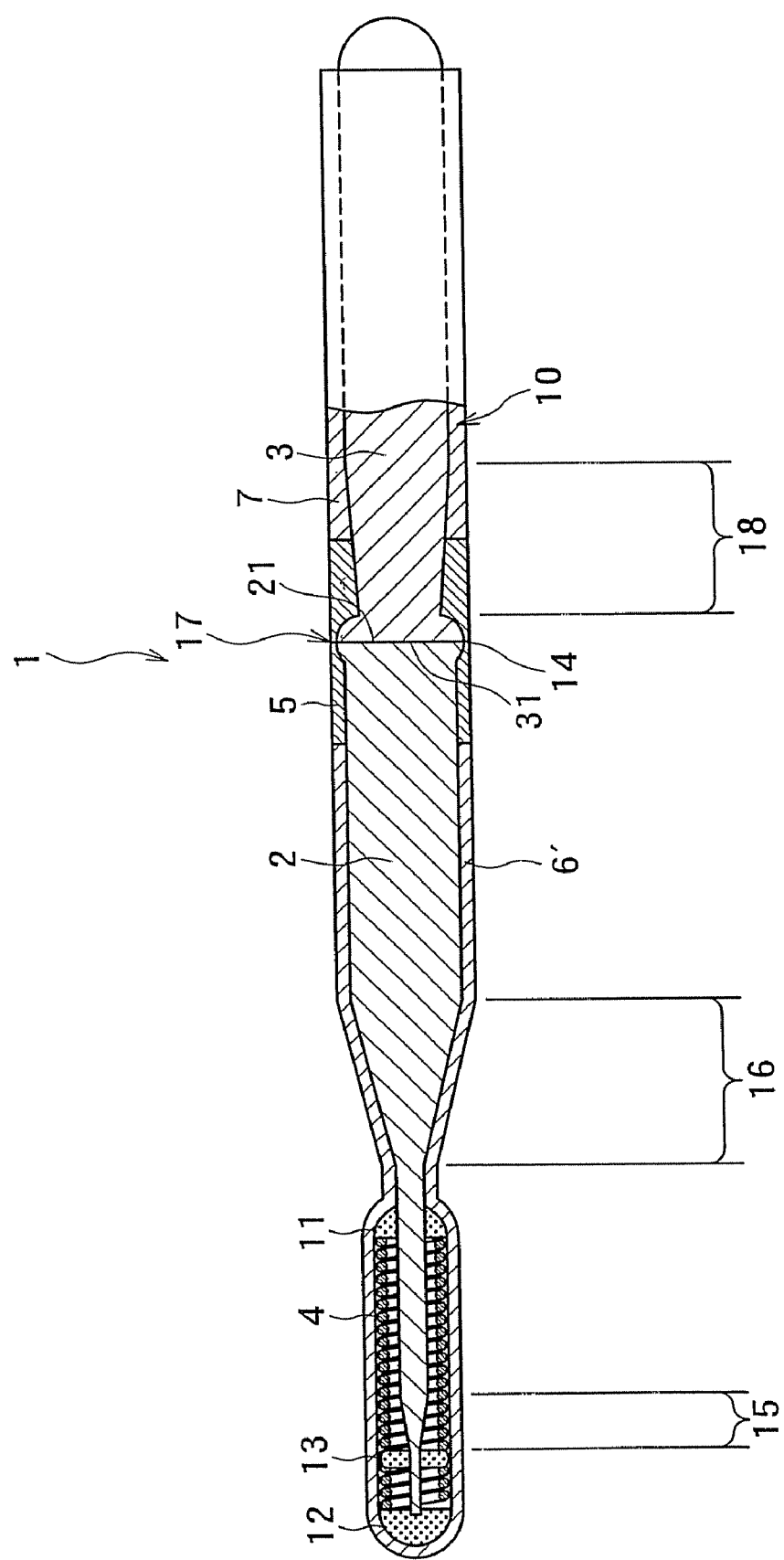
FIG. 5 is a longitudinal sectional view showing a fourth embodiment of the guide wire of the present invention.

FIG. 5 is a longitudinal sectional view showing a fourth embodiment of the guide wire of the present invention. The fourth embodiment of the guidewire of the present invention will be described with reference to FIG. 5, principally, about differences from the previous embodiments, with the description of the same features omitted.

According to a guide wire 1 in this embodiment, a cover layer 5 is formed so as to cover the vicinity of a welded portion 14 of a wire member 10, a distal-side cover layer 6' different from the cover layer 5 is formed on the distal side from the cover layer 5, and a proximal-side cover layer 7 different from the cover layer 5 is formed on the proximal side from the cover layer 5.

The distal-side cover layer 6' may be made from a material selected from the materials used for forming the cover layer 5 and the second cover layer 6 in the previous embodiments. The material for forming the distal-side cover layer 6' may be identical to or different from that of each of the cover layer 5 and the proximal-side cover layer 7.

The material of the proximal-side cover layer 7 is not particularly limited but may be selected from the materials used for forming the cover layer 5 and the distal-side cover layer 6' and other materials. The material of the proximal-side cover layer 7 may be identical to or different from the material used for forming each of the cover layer 5 and the distal-side cover layer 6'.

The proximal-side cover layer 7 may be made from any material as described above, but is preferably made from a fluorocarbon resin or a composite material thereof. This makes it possible to effectively reduce the friction resistance (sliding resistance) of the guide wire 1 against the inner wall of a catheter and improve the sliding performance, and hence to enhance the operationality of the guide wire 1 in the catheter. Further, in the case of moving and/or rotating the guide wire 1 in the catheter, it is possible to more certainly prevent kink (sharp bending) or torsion of the guide wire 1, particularly, in the vicinity of the welded portion.

The materials of the cover layer 5, the distal-side cover layer 6', and the proximal-side cover layer 7 are preferably set such that the cover layer 5 be made from a silicone resin or a composite material thereof, the distal-side cover layer 6' be made from a fluorocarbon resin or a composite material thereof, and the proximal-side cover layer 7 be made from a fluorocarbon resin or a composite material thereof.

With this configuration, it is possible to combine the above-described advantage obtained by the use of a silicone resin with the above-described advantage obtained by the use of a fluorocarbon resin. Concretely, by adopting such a combination of the materials of the cover layer 5, the distal-side cover layer 6', and the proximal-side cover layer 7, it is possible to obtain a sufficient sliding performance of the entire guide wire 1 while keeping the joining strength of the welded portion 14 between the first wire 2 and the second wire 3, and hence to enhance the operationality of the guide wire 1.

In the case of using the above-described combination of the materials for forming the cover layer 5, the distal-side cover layer 6', and the proximal-side cover layer 7, as described above, it is preferred that the wire member 10 be not heated for forming the cover layer 5 and be heated for forming each of the distal-side cover layer 6' and the proximal-side cover layer 7. With this configuration, it is possible to make the above-described effect significant and to enhance the adhesion of each of the distal-side cover layer 6' and the proximal-side cover layer 7 on the wire member 10.

The thickness (in average) of the distal-side cover layer 6' is not particularly limited but is preferably in a range of about 1 to 20 µm, more preferably, about 2 to 10 µm. The thickness of the distal-side cover layer 6' may be identical to or different from each of the thickness of the cover layer 5 and the thickness of the proximal-side cover layer 7.

The thickness (in average) of the proximal-side cover layer 7 is not particularly limited but is preferably in a range of about 1 to 20 µm, more preferably, about 2 to 10 µm. The thickness of the proximal-side cover layer 7 may be identical to or different from each of the thickness of the cover layer 5 and the thickness of the distal-side cover layer 6'.

In the configuration shown in FIG. 5, the proximal end of the cover layer 5 is joined to the distal end of the proximal-side cover layer 7, and is therefore continuous thereto; the proximal end of the cover layer 5 may be separated from the distal end of the proximal-side cover layer 7, or the cover layer 5 may be partially overlapped to the proximal-side cover layer 7.

In this embodiment, the distal-side cover layer 6' covers the coil 4; however, the coil 4 may be covered with a different material, for example, a hydrophilic material.

Figure 6:
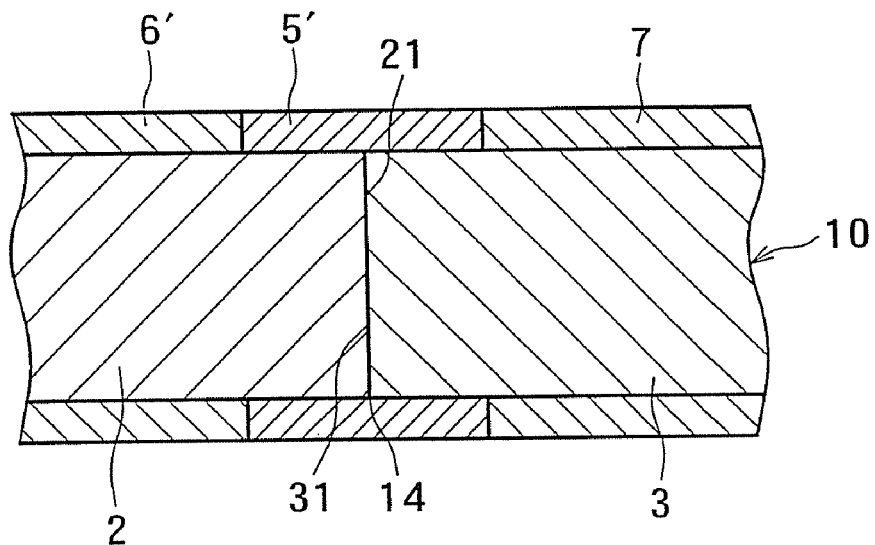
FIG. 6 is a longitudinal sectional view showing a modification of a portion, in the vicinity of a welded portion, of the guide wire of the present invention.
Figure 7:
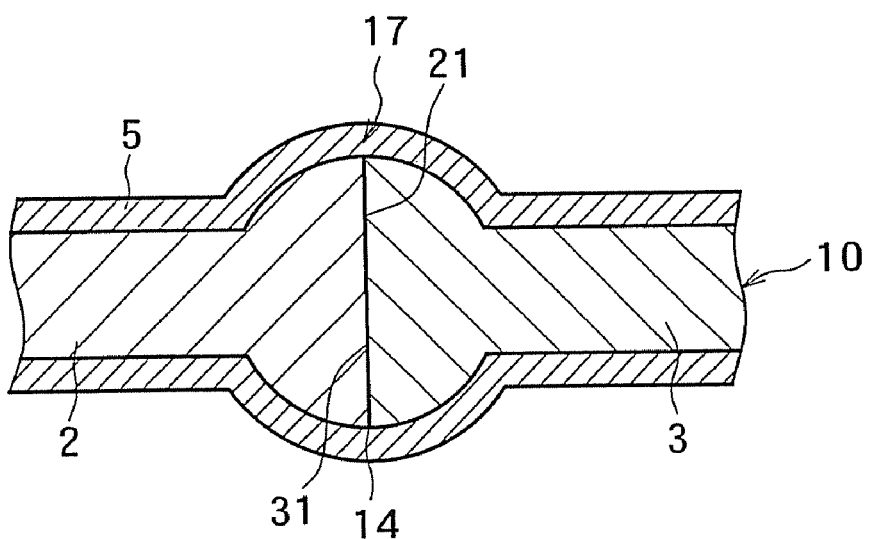
FIG. 7 is a longitudinal sectional view showing another modification of the portion, in the vicinity of a welded portion, of the guide wire of the present invention.

FIGS. 6 and 7 are longitudinal sectional views showing modifications of a portion, in the vicinity of the welded portion, of the guide wire of the present invention.

As shown in FIG. 6, a cover layer 5' is formed on the outer periphery of a portion, in the vicinity of a welded portion 14, of a wire member 10 in such a manner as to cover the outer periphery of the welded portion 14, that is, to cross the welded portion 14. Like the above-described configuration, a distal-side cover layer 6' and a proximal-side cover layer 7 are formed on the distal side and the proximal side from the cover layer 5', respectively. In this case, the thickness of the cover layer 5' is nearly uniform in the axial direction.

The cover layer 5' functions as a reinforcing layer for reinforcing the welded portion 14. The provision of such a cover layer 5' is effective to improve the welding strength of the welded portion 14. As a result, in the case of applying a torsional torque or a pushing force from the second wire 3 to the first wire 2, it is possible to prevent deformation and breakage of the welded portion 14, and hence to more certainly transmit the torsional torque or pushing force.

The cover layer 5' may be made from a material selected from metal materials and resin materials. In particular, a metal material is preferably used.

The cover layer 5' is preferably made from a material having a rigidity equal to or smaller than that of the above-described material for forming the first wire 2, that is, having a flexibility equal to or larger than that of the material for forming the first wire 2. With this configuration, it is possible to obtain the advantage by the above-described reinforcing effect while sufficiently ensuring the flexibility and restoring performance against bending in the vicinity of the welded portion 14.

A projection 17 projecting in the outer peripheral direction is formed on a welded portion 14 shown in FIG. 7. The effect obtained by formation of the projection 17, and the condition and forming method of the projection 17 may be the same as those described above.

A cover layer 5 similar to that described above is provided on the outer periphery of a wire member 10. In this case, the cover layer 5 is formed so as to cross the projection 17, that is, cross the welded portion 14. The thickness of the cover layer 5 is nearly uniform from the proximal end to the distal end of the projection 17. With this configuration, it is possible to sufficiently ensure the flexibility and restoring performance against bending in the vicinity of the welded portion 14.

In the configuration shown in FIGS. 4, 5, and 7, each of one side (upper side in the figure) and the other side (lower side in the figure) of the projection 17 is formed into an approximately circular-arc shape in longitudinal cross-section, and the welded portion 14 is located on the maximum outer-diameter portion of the projection 17. This is advantageous in enlarging an area of the welded surface of the welded portion 14, thereby obtaining a higher joining strength (welding strength).

According to the present invention, the shape of the projection 17 and the position of the welded portion 14 relative to the projection 17 are not limited to those described above. For example, each of one side and the other side of the projection 17 may be formed into a non-circular (non-circular arc) such as a trapezoidal or triangular shape in longitudinal cross-section. The proximal side and the distal side of the projection 17 may be formed into shapes asymmetric to each other with respect to the welded surface (connection end face 21, 31) of the welded portion 14. The axial position of the welded surface of the welded portion 14 relative to the projection 17 is not necessarily located at the central portion as shown in FIGS. 4, 5, and 7 but may be located at a position offset to the proximal side (second wire 3 side) or on the distal side (first wire 2 side). With this configuration, it is possible to prevent or relieve stress concentration at the welded portion 14, and hence to more certainly prevent breakage of the welded portion 14 due to stress concentration at the welded portion 14 when a torsional torque or pushing force is applied from the second wire 3 to the first wire 2.

The cover layer 5 covering the projection 17 may be configured as the reinforcing layer described in the embodiment shown in FIG. 6. In the case of covering the projection 17 with a metal material, the joining strength of the projection 17 can be improved. For example, by inserting a relatively thin metal tube to a portion near the projection 17 and applying a pressure to the metal tube from external, the cover layer 5 strongly adhering on the projection 17 can be formed.

Figure 8:
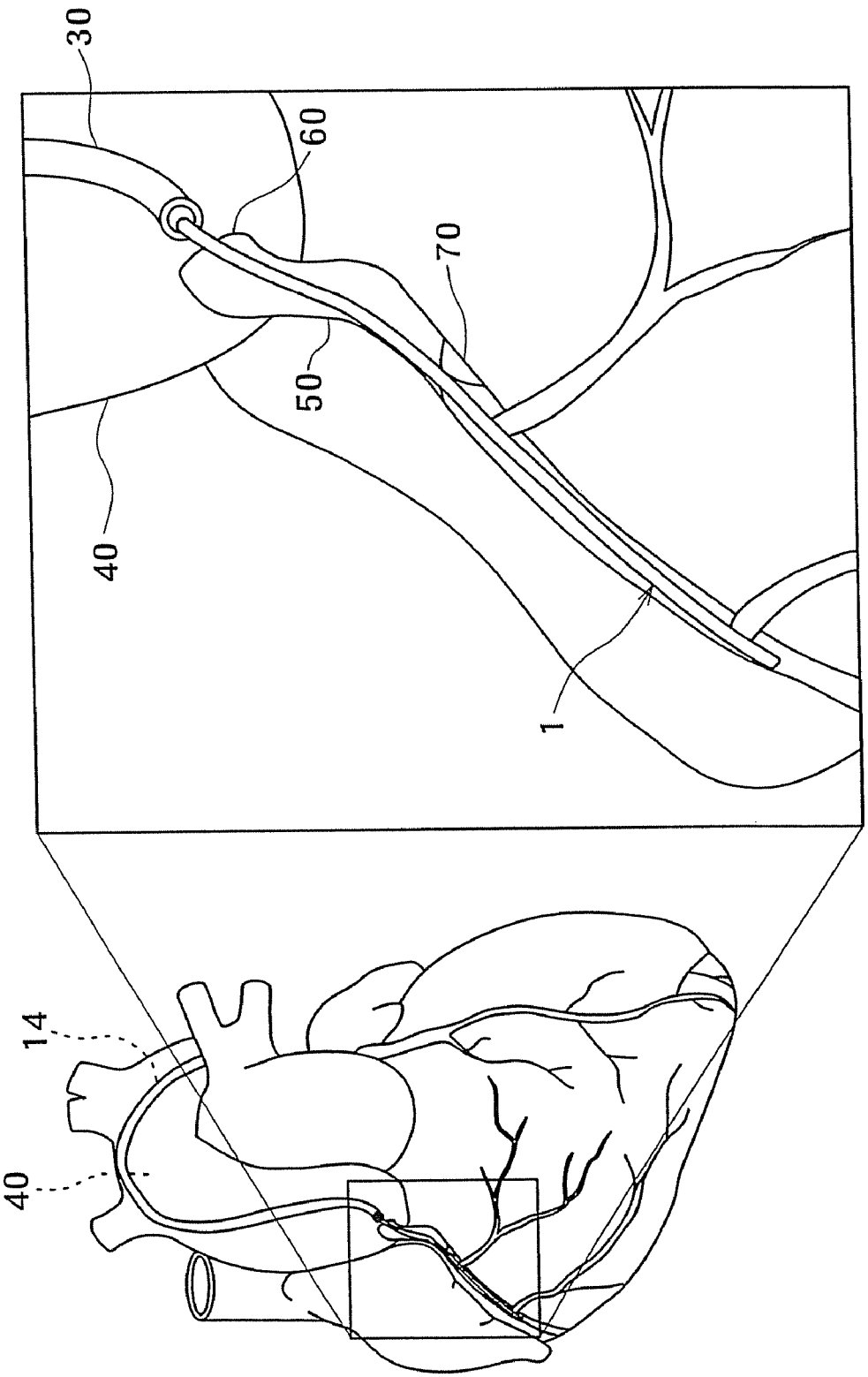
FIG. 8 is a typical view illustrating an example of how to use the guide wire of the present invention.

FIGS. 8 and 9 are views showing the operational state of the guide wire 1 of the present invention during use in the PTCA process.

In FIGS. 8 and 9, reference numeral 40 denotes an aortic arch, 50 is a right coronary artery of a heart, 60 is an ostium of the right coronary artery 50, and 70 is a target angiostenosis portion. Further, reference numeral 30 denotes a guiding catheter for certainly guiding the guide wire 1 from an arteria fermoralis into the right coronary artery 50, and 20 is a balloon catheter having at its distal end an expandable and contractible balloon 201 for dilating the target angiostenosis portion 70.

As shown in FIG. 8, the guide wire 1 is moved in such a manner that the distal end thereof projecting from the distal end of the guiding catheter 30 is inserted in the right coronary artery 50 through the ostium 60 of the right coronary artery 50. The guide wire 1 is further advanced, and is stopped when the distal end thereof passes the target angiostenosis portion 70 in the right coronary artery 50. In this state, an advance path of the balloon catheter 20 is ensured. At this time, the welded portion 14 of the guide wire 1 is located in the living body, more specifically, in the vicinity of the distal portion of the aortic arch 40.

As shown in FIG. 9, the balloon catheter 20 is inserted around the guide wire 1 from the proximal side of the guide wire 1. The balloon catheter 20 is then advanced in such a manner that the distal end thereof projects from the distal end of the guiding catheter 30, goes ahead along the guide wire 1, and enters the right coronary artery 50 from the ostium 60 of the right coronary artery 50. The balloon catheter 20 is stopped when the balloon 201 reaches a position corresponding to that of the target angiostenosis portion 70.

A fluid for inflating the balloon 201 is injected in the balloon catheter 20 from the proximal side of the balloon catheter 20, to inflate the balloon 201, thereby dilating the target angiostenosis portion 70. As a result, deposits such as cholesterol adhering on the arterial wall of the target angiostenosis portion 70 are physically compressed against the arterial wall, to eliminate blocking of blood flow.

In the above-described embodiments, each of the composing elements of the guide wire may be replaced with a composing element having any other configuration exhibiting the similar effect, and may be provided with any other additional element.

While the preferred embodiments of the present invention have been described using specific terms, such description is for illustrative purposes only, and it is to be understood that changes and variations may be made without departing from the spirit or scope of the following claims.

What is claimed is:

1. A guide wire comprising:
   a wire member including a first wire disposed on a distal side of said wire member and a second wire disposed on a proximal side from said first wire,
   the first wire and the second wire each possessing an end face, the end face of the first wire and the end face of the second wire being welded to one another at a welded portion so that the first and second wires do not axially overlap one another;
   a cover layer provided on an outer periphery of said wire member and covering said welded portion between said first wire and said second wire;
   the cover layer is made of a resin material that reduces friction;
   a proximal-side cover layer disposed on the proximal side from the cover layer without an axial gap between the cover layer and the proximal-side cover layer, the cover layer and the proximal-side cover layer do not axially overlap one another;
   a distal-side cover layer disposed on the distal side from the cover layer without an axial gap between the cover layer and the distal-side cover layer, the cover layer and the distal-side cover layer do not axially overlap one another;
   wherein the cover layer is formed such that the wire member is not heated at a time of covering the wire member with the cover layer; and
   wherein the wire member is directly heated to form the proximal-side cover layer and the distal-side cover layer.

2. A guide wire according to claim 1, wherein the cover layer covering the welded portion is made from a fluorocarbon resin or hydrophilic material.

3. A guide wire according to claim 1, wherein the cover layer covering the welded portion is made from a silicone resin.

4. A guide wire according to claim 1, wherein the cover layer covering the welded portion is made from a metal having an elastic modulus that is equal to or smaller than that of the first wire.

5. A guide wire according to claim 1, wherein a thickness of the cover layer covering the welded portion is within the range of 1 to 2 μm and is uniform throughout the cover layer.

6. A guide wire according to claim 1, wherein a thickness of the cover layer covering the welded portion is uniform.

7. A guide wire according to claim 1, wherein the cover layer extends across the welded portion and has a thickness that is uniform from a proximal end of the welded portion to a distal end of the welded portion.

8. A guide wire according to claim 1, wherein the first wire is made from a superelastic alloy and the second wire is made from stainless steel.

9. A guide wire according to claim 1, wherein the second wire is made from a Co-based alloy and the Co-based alloy is a Co—Ni—Cr alloy.

10. A guide wire according to claim 1, wherein the end face of the first wire and the end face of the second wire at which the first and second wires and welded are each perpendicular to an axial direction of the first and second wires, and the welding between the first and second end faces is performed by a butt resistance welding process.

11. A guide wire according to claim 1, wherein the distal-side cover layer is made from a material that reduces friction of the distal-side cover layer.

12. A guide wire according to claim 1, wherein the distal-side cover layer is made from a fluorocarbon resin or hydrophilic material.

13. A guide wire according to claim 1, wherein an average thickness of the distal-side cover layer is in a range of 1 to 20 μm.

14. A guide wire according to claim 1, wherein the second wire is made from a material having an elastic modulus larger than that of the first wire.

15. A guide wire according to claim 1, wherein the distal-side cover layer is formed such that the wire member is heated at a time when the wire member is covered by the distal-side cover layer.

16. The guide wire according to claim 1, wherein a connection end face of the first wire and a connection end face of the second wire are welded; and
   said connection end faces are formed into a recessed and raised shape, respectively.

17. The guide wire according to claim 1, wherein said cover layer is made from a reaction-curing type of the resin material or a composite material thereof, and a formation of the cover layer is performed at room temperature.

18. The guide wire according to claim 1, wherein an entire outer surface of the cover layer is devoid of grooves.

19. The guide wire according to claim 1, wherein the distal-side cover layer is separate from the cover layer, with a joint between a proximal end of the distal-side cover layer and a distal end of the cover layer, the joint being positioned about a tapered portion of the first wire.

20. A guide wire comprising:
   a wire member including a first wire disposed on a distal side of said wire member and a second wire disposed on a proximal side from said first wire,
   the first wire and the second wire each possessing an end face, the end face of the first wire and the end face of the second wire being welded to one another at a welded portion so that the first and second wires do not axially overlap one another;
   a cover layer provided on an outer periphery of said wire member and covering said welded portion between said first wire and said second wire;
   the cover layer is made of a resin material that reduces friction;
   a proximal-side cover layer disposed on the proximal side from the cover layer without an axial gap between the cover layer and the proximal-side cover layer, the cover layer and the proximal-side cover layer do not axially overlap one another; and
   a distal-side cover layer disposed on the distal side from the cover layer without an axial gap between the cover layer and the distal-side cover layer, the cover layer and the distal-side cover layer do not axially overlap one another;
   wherein the cover layer is formed such that the wire member is not heated at a time of covering the wire member with the cover layer; and
   wherein the proximal-side cover layer and the distal-side cover layer are made of a fluorocarbon resin, and the cover layer covering the welded portion is made from a silicone.

21. A guide wire comprising:
   a wire member including a first wire disposed on a distal side of said wire member and a second wire disposed on a proximal side from said first wire,
   the first wire and the second wire each possessing an end face, the end face of the first wire and the end face of the second wire being welded to one another at a welded portion so that the first and second wires do not axially overlap one another;

a cover layer provided on an outer periphery of said wire member and covering said welded portion between said first wire and said second wire;

the cover layer is made of a resin material that reduces friction;

a proximal-side cover layer disposed on the proximal side from the cover layer without an axial gap between the cover layer and the proximal-side cover layer, the cover layer and the proximal-side cover layer do not axially overlap one another;

a distal-side cover layer disposed on the distal side from the cover layer without an axial gap between the cover layer and the distal-side cover layer, the cover layer and the distal-side cover layer do not axially overlap one another;

wherein the cover layer is formed such that the wire member is not heated at a time of covering the wire member with the cover layer;

wherein the welded portion has a projection projecting in the outer peripheral direction; and wherein the cover layer covers the projection so that the cover layer has an outer surface without a bump at the projection of the welded portion.

* * * * *